United States Patent
Tsukerman

(10) Patent No.: US 8,859,974 B2
(45) Date of Patent: Oct. 14, 2014

(54) ADJUSTABLE SPECT DETECTOR

(75) Inventor: Leonid Tsukerman, Kiryat Mozkin (IL)

(73) Assignee: General Electric Company, Schenectady, NY (US)

( * ) Notice: Subject to any disclaimer, the term of this patent is extended or adjusted under 35 U.S.C. 154(b) by 886 days.

(21) Appl. No.: 12/970,397

(22) Filed: Dec. 16, 2010

(65) Prior Publication Data

US 2012/0153176 A1 Jun. 21, 2012

(51) Int. Cl.
*G01T 1/166* (2006.01)
*G01T 1/29* (2006.01)

(52) U.S. Cl.
CPC .................................. *G01T 1/2985* (2013.01)
USPC .................................................... 250/363.05

(58) Field of Classification Search
USPC .................................................... 250/363.05
See application file for complete search history.

(56) References Cited

U.S. PATENT DOCUMENTS

| | | | | |
|---|---|---|---|---|
| 4,582,994 A | * | 4/1986 | Berg | 250/363.1 |
| 4,731,536 A | * | 3/1988 | Rische et al. | 250/394 |
| 5,717,212 A | * | 2/1998 | Fulton et al. | 250/363.05 |
| 5,939,724 A | * | 8/1999 | Eisen et al. | 250/370.09 |
| 6,055,450 A | * | 4/2000 | Ashburn | 600/431 |
| 6,114,701 A | * | 9/2000 | Plummer et al. | 250/363.05 |
| 6,147,353 A | * | 11/2000 | Gagnon et al. | 250/363.05 |
| RE38,560 E | * | 8/2004 | Hug et al. | 250/363.08 |
| 2004/0251419 A1 | * | 12/2004 | Nelson et al. | 250/370.09 |
| 2008/0001088 A1 | * | 1/2008 | Joung | 250/363.1 |
| 2008/0029704 A1 | * | 2/2008 | Hefetz et al. | 250/363.01 |
| 2010/0001192 A1 | * | 1/2010 | Lange et al. | 250/363.1 |
| 2010/0193696 A1 | | 8/2010 | Blevis et al. | |

\* cited by examiner

*Primary Examiner* — David Porta
*Assistant Examiner* — Mindy Vu
(74) *Attorney, Agent, or Firm* — Fletcher Yoder, P.C.

(57) ABSTRACT

A SPECT detector system includes a plurality of detector units. Each detector unit includes a plurality of detector elements disposed in fixed positions with respect to one another. The detector units are adjustably positioned with respect to one another around a detector arc, which is placed adjacent to a patient.

20 Claims, 4 Drawing Sheets

ADJUSTABLE SPECT DETECTOR

BACKGROUND OF THE INVENTION

The subject matter disclosed herein relates to single photon emission computed tomography (SPECT), and more particularly to adjustable SPECT detectors.

A wide range of imaging techniques are known and currently in use, particularly for medical diagnostic applications. One such technique, SPECT, relies on the emission of gamma rays during the radioactive decay of a radioisotope (or radionuclide), commonly administered in the form of a radiopharmaceutical agent that can be carried, and in some cases, bound to particular tissues of interest. A SPECT scanner detects the emissions via a gamma radiation detector that typically includes a collimator, a scintillator, and a series of photomultiplier tubes. The collimator allows only emissions in a particular direction to enter into the scintillator. The scintillator converts the gamma radiation into lower energy ultraviolet photons that are detected by the photomultiplier tubes. These, in turn, generate image data related to the quantity of radiation impacting the individual regions. Image reconstruction techniques, such as back projection, may then be used to reconstruct images of internal structures of the subject based upon this image data.

While such systems have proven extremely useful at providing high quality images with good diagnostic value, further refinement is needed. For example, existing SPECT scanners may include one or more detectors that are rotated about the subject. Such systems may be complicated and costly because of the need for electro-mechanical components to rotate the detectors. In addition, some subjects may not be comfortable with having detectors moving around them. Furthermore, existing SPECT detectors may be flat and relatively large to be able to image a wide range of subjects. However, because of the irregular shape of subjects, only a small portion of such SPECT detectors may be brought into close proximity with the subject. Peripheral areas of these SPECT detectors may provide lower quality images of the subject. Smaller SPECT detectors may address some of these issues, but such detectors may lack a large field of view. For example, small SPECT detectors may not be capable of imaging an entire subject at once. Thus, some subjects may be made uncomfortable by the increased imaging time made necessary by small SPECT detectors. Improved SPECT scanners are needed that will permit high quality imaging of large fields of view of a variety of subject sizes and avoid such drawbacks in the prior art.

BRIEF DESCRIPTION OF THE INVENTION

The present invention provides novel techniques for SPECT detector systems. In particular, embodiments of the SPECT detector system include adjustable components to enable the SPECT detector system to conform to a variety of subjects. More particularly, in various embodiments, detector elements may be adjustably positioned with respect to one another around a detector arc. The detector arc may be adjusted to conform to the shape of the subject, such that a field of view of the SPECT detector system covers the entire subject to be imaged. In addition, the detector arc may remain stationary during imaging. Although discussed with respect to SPECT detector systems, it should be borne in mind that the invention may be applied in a wide range of contexts, in a variety of imaging systems, and in any desired industrial, commercial, private, or other setting.

In accordance with one aspect of the present disclosure, a SPECT detector system includes a plurality of detector units. Each detector unit includes a plurality of detector elements disposed in fixed positions with respect to one another. The detector units are adjustably positioned with respect to one another around a detector arc.

In accordance with another aspect, a SPECT detector system includes a gamma ray detector, which includes a plurality of detector units. Each detector unit includes a plurality of detector elements disposed in fixed positions with respect to one another. The detector units are adjustably positioned with respect to one another around a detector arc. The detector elements of each detector unit are disposed to produce a field of view that covers an entire subject to be imaged. The SPECT detector system also includes an image data processing component that receives image data from the detector and generates an image based upon the image data.

In accordance with a further aspect, a SPECT detector system includes a plurality of detector components, which are adjustably positioned with respect to one another around a detector arc.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
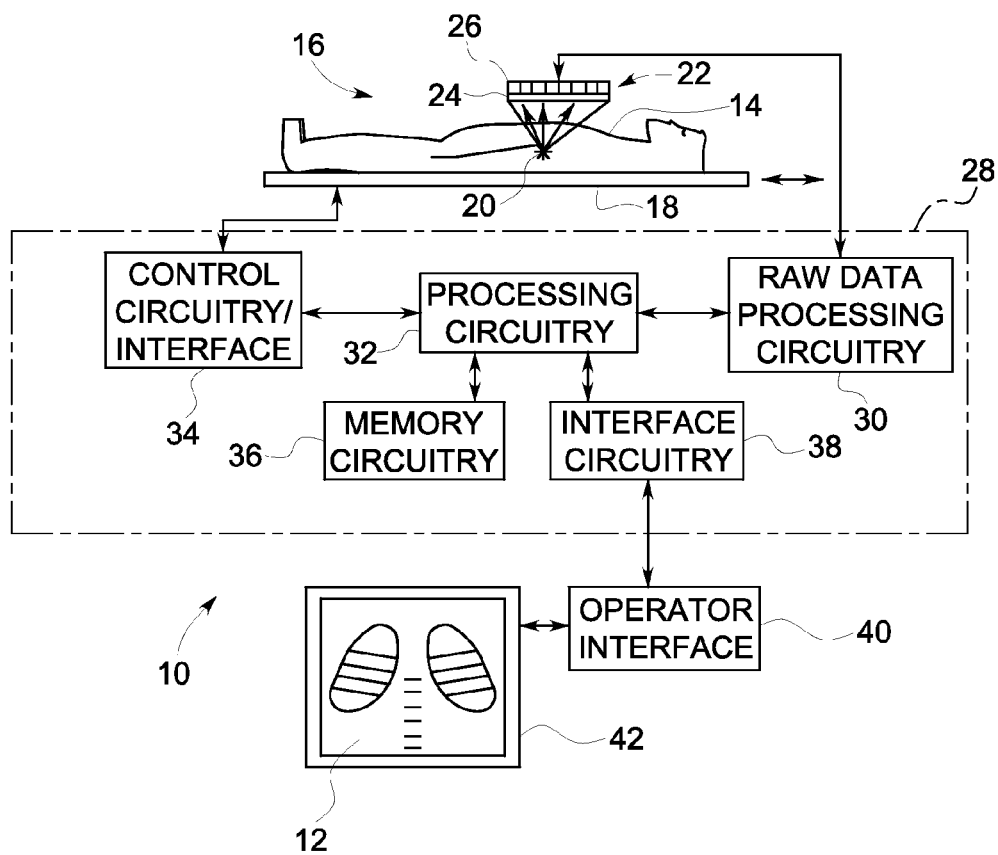
FIG. 1 is a diagrammatical representation of an exemplary SPECT imaging system incorporating aspects of the present techniques.

A diagrammatic representation of an exemplary SPECT imaging system is shown in FIG. 1. The system, designated generally by the reference numeral 10, is designed to produce useful images 12 of a subject 14 using adjustable detector arcs as described in detail below. The subject is positioned in a scanner, designated by reference numeral 16, in which a patient support 18 is positioned. The support may be movable within the scanner to allow for imaging of different tissues or anatomies of interest 20 within the subject. Prior to image data collection, a radioisotope, such as a radiopharmaceutical substance (sometimes referred to as a radiotracer), is administered to the patient, and may be bound or taken up by particular tissues or organs 20. Typical radioisotopes include various radioactive forms of elements, although many in SPECT imaging are based upon an isotope of technetium ($^{99}$Tc) that emits gamma radiation during decay. Various additional substances may be selectively combined with such radioisotopes to target specific areas or tissues 20 of the body.

Gamma radiation emitted by the radioisotope is detected by a digital detector or gamma camera 22. Although illustrated in the figure as a planar device positioned above the patient, in practice the camera may be positioned below the patient, both above and below the patient, and may wrap at least partially around the patient. In general, the gamma camera 22 includes one or more gamma radiation sensors. In the illustrated embodiment, the gamma radiation sensor comprises one or more collimators and a scintillator, together represented generally as reference numeral 24. The collimator allows gamma radiation emitted only in certain directions (typically perpendicular to the scintillator) to impact the scintillator. The scintillator, which is typically made of a crystalline material, such as sodium iodide (NaI), converts the received gamma radiation to lower energy light energy (e.g., in an ultraviolet range). Photomultiplier tubes 26 then receive this light and generate image data corresponding to photons impacting specific discrete picture element (pixel) regions. In other embodiments, the gamma radiation sensor may not include the scintillator and photomultiplier tubes 26, but instead use other gamma radiation sensing technologies.

The gamma camera is coupled to system control and processing circuitry 28. This circuitry may include a number of physical and functional components that cooperate to allow the collection and processing of image data to create the desired images. For example, the circuitry may include raw data processing circuitry 30 that initially receives the data from the gamma camera, and that may perform various filtering, value adjustments, and so forth. Processing circuitry 32 allows for the overall control of the imaging system, and for manipulation of image data. The processing circuitry 32 may also perform calibration functions, correction functions, and so forth on the data. The processing circuitry 32 may also perform image reconstruction functions, such as based on known algorithms (e.g., back projection). Such functions may also be performed in post-processing on local or remote equipment (not shown). The processing circuitry may interact with control circuitry/interface 34 that allows for control of the scanner and its components, including the patient support, camera, and so forth. Moreover, the processing circuitry 32 will be supported by various circuits, such as memory circuitry 36 that may be used to store image data, calibration or correction values, routines performed by the processing circuitry, and so forth. Finally, the processing circuitry may interact with interface circuitry 38 designed to support an operator interface 40. The operator interface allows for imaging sequences to be commanded, scanner and system settings to be viewed and adjusted, images to be viewed, and so forth. In the illustrated embodiment, the operator interface includes a monitor 42 on which reconstructed images 12 may be viewed.

In an institutional setting, the imaging system 10 may be coupled to one or more networks to allow for the transfer of system data to and from the imaging system, as well as to permit transmission and storage of image data and processed images. For example, local area networks, wide area networks, wireless networks, and so forth may allow for storage of image data on radiology department information systems or on hospital information systems. Such network connections further allow for transmission of image data to remote post-processing systems, physician offices, and so forth.

Figure 2:
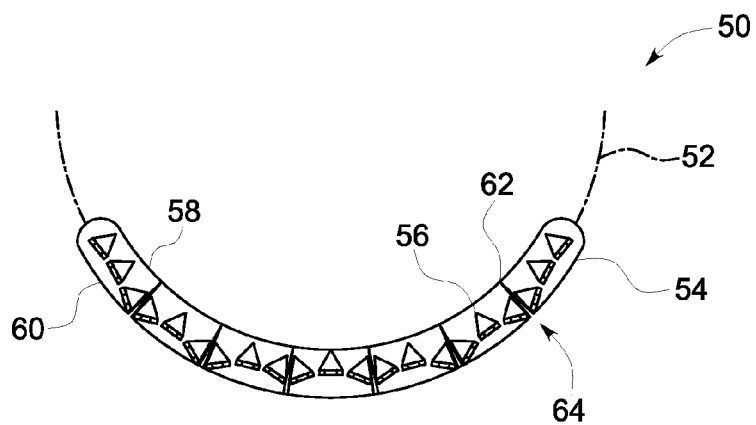
FIG. 2 is a cross-sectional view of an exemplary detector arc.

FIG. 2 illustrates an exemplary detector arc 50, or gamma ray detector, which may be used as the digital detector or gamma camera 22 in FIG. 1. As described in detail below, the detector arc 50 is stationary during imaging of the subject 14.

Use of a stationary detector arc 50 provides for simultaneous 3D acquisition of the gamma radiation emitted from the subject 14 in all directions, which helps to reduce image artifacts caused by motion of the subject 14. In addition, simultaneous 3D acquisition provides for dynamic imaging of physiological processes in the subject 14, such as cardiac blood flow dynamics. Further, the shape of the detector arc 50 generally follows the contours of an arc 52. The arc 52 may be a circular arc, an oval arc, or any other segment of a curve. The shape of the arc 52, and correspondingly the shape of the detector arc 50, is selected to generally conform to the contours of the subject 14. In the particular embodiment shown, the detector arc 50 includes a plurality of interconnected detector units 54, which enable the detector arc 50 to adjust to the subject 14. In other words, the detector units 54 are adjustably positioned with respect to one another around the detector arc 50. Each of the detector units 54 may include one or more detector elements 56 disposed in fixed positions with respect to one another. Although each of the detector units 54 shown in FIG. 2 includes the same number of detector elements 56, in other embodiments, the number of detector elements 56 may vary in the detector units 54. For example, the detector units 54 located near the ends of the detector arc 50 may include fewer detector elements 56 than the detector units 54 near the middle of the detector arc 50. Such a configuration of the detector arc 52 may enable more curvature near the ends of the detector arc 50 compared to the middle of the detector arc 50. In the illustrated embodiment, the detector arc 50 includes an inner surface 58, which faces the subject 14, and an outer surface 60, which faces away from the subject 14. The detector elements 56 are configured to point toward the inner surface 58. Furthermore, the detector units 54 are interconnected by hinges 62, which enable each of the detector units 54 to move independently of the other detector units 54. The hinge 62 may be made of a flexible material or of two or more moving components. Gaps 64 are provided between the detector units 54 to enable movement of the detector units 54 toward the subject 14. In the illustrated embodiment, the width of the gaps 64 increases moving toward the outer surface 60 of the detector arc 50.

Figure 3:
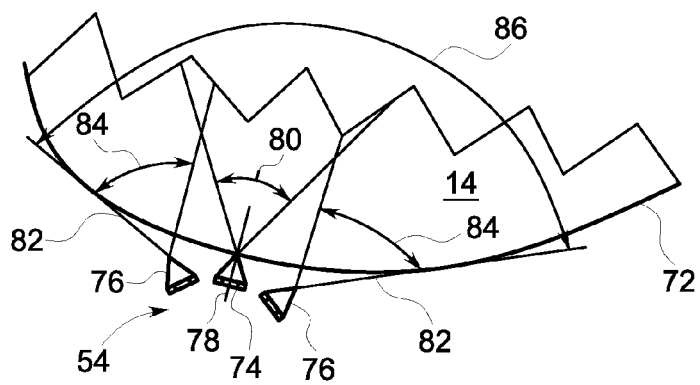
FIG. 3 is a cross-sectional view of an exemplary detector unit placed adjacent to a subject.

FIG. 3 illustrates a cross-sectional view of one detector unit 54 adjacent to the subject 14. Specifically, the detector unit 54 is placed adjacent to an external surface 72 of the subject 14. In the illustrated embodiment, the detector unit 54 includes an inner detector element 74 and two outer detector elements 76. An axis 78 bisects or passes through the middle of the inner detector element 74. As shown in FIG. 3, the axis 78 is perpendicular to the external surface 72 at a point where the inner detector element 74 is adjacent to the external surface 72. In other words, the inner detector element 78 is normal to the external surface 72. Furthermore, the other detector units 54 of the detector arc 50 are also configured such that the inner detector elements 78 are normal to the external surface 72. The inner detector element 78 has a field of view as indicated by angle 80. In general, the field of view of a detector element represents the extent of the subject 14 that is detectable by the detector element.

The outer detector elements 76 shown in FIG. 3 are configured such that an angular limit 82 of the field of view is at least tangential to the external surface 72. In other words, the outer detector elements 76 are configured to include as much of the subject 14 in the field of view of as possible, and in presently contemplated embodiments, the combined elements of each unit includes the entire subject in the field of view of the unit. The field of view of the outer detector elements 76 is indicated by angle 84, which may be smaller or larger than the field of view angle 80 of the inner detector element 74. The field of view angles 80 and 84 may depend on the type of detector element selected, and may be adjustable in some embodiments. In addition, in certain embodiments, the field of view angles 80 and 84 may not all be the same. For example, in certain embodiments, the detector elements of at least two of the detector units 54 may have different field of view angles. As shown in FIG. 3, the fields of view 80 and 84 of the inner detector element 74 and the outer detector elements 76 combine to produce a detector unit field of view, indicated by angle 86, which includes the entire subject 14. Thus, each of the detector unit fields of view 86 of the detector arc 50 covers the entire subject 14 to be imaged. In certain embodiments, the detector units 54 of the detector arc 50 are positioned to provide at least approximately 180 degree coverage for every volume element of the subject 14. In other words, the positioning of the detector units 54 provides optimal angular coverage, angular sampling, spatial resolution, and sensitivity for every volume element of the imaged subject 14. Furthermore, in certain embodiments, the detector unit field of view 86 may be adjustable. For example, one or more of the detector elements may be adjustable, thus adjusting the detector unit field of view 86.

Figure 4:
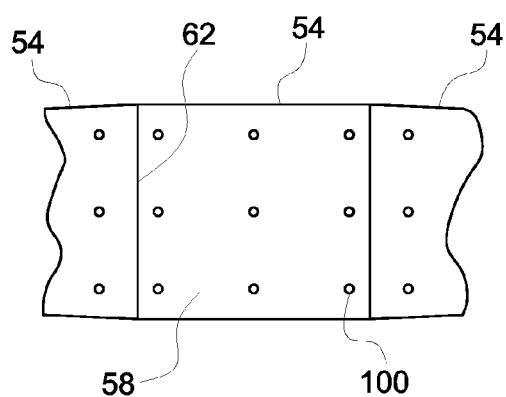
FIG. 4 is an axial coronal view of a portion of an exemplary detector arc.

FIG. 4 illustrates an axial coronal view of a portion of the detector arc 50. Specifically, FIG. 4 shows one complete detector unit 54 and two adjacent partial detector units 54. The detector units 54 are interconnected by the hinges 62. In addition, the inner surface 58 of the detector units 54 includes openings 100, or apertures, for each of the detector elements 56. In the illustrated embodiment, the openings 100 are circular-shaped. In other embodiments, the shape of the openings 100 may be different depending on the particular style of detector elements 56 used in the detector arc 50. The number of detector elements 56 in each detector unit 54 may vary depending on the location of the detector unit 54 in the detector arc 50 and the extent of coverage desired of the subject 14. For example, a wider detector unit 54 may be used to provide additional coverage of the subject 14.

Figure 5:
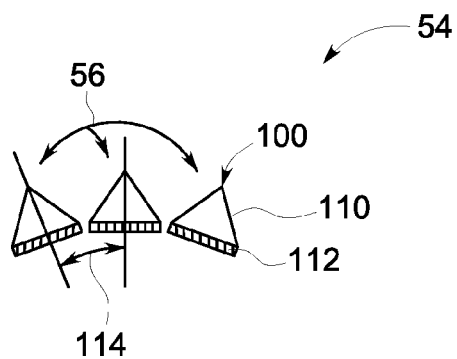
FIG. 5 is a transaxial view of an exemplary detector unit.

FIG. 5 illustrates a transaxial view of an embodiment of the detector unit 54 that includes three detector elements 56. Other embodiments of the detector unit 54 may include more or fewer detector elements 56 depending on the needs of a particular configuration. For example, detector units 54 with fewer detector elements 56 may be better able to conform to the external surface 72 of the subject 14 because the detector units 54 are smaller. In the illustrated embodiment, the detector elements 56 include pinhole collimators 110, which are designed such that only gamma rays traveling in certain directions impact a detector assembly 112, which includes the gamma radiation sensor described in detail above. The detector assembly 112 may also be referred to as a gamma ray sensor. Gamma rays passing through the openings 100 generally project an inverted image of a source onto the detector assembly 112. The opening 100 is disposed at the tip of the pinhole collimator 110 and faces toward the subject 14. A cross-sectional shape of the pinhole collimator 110 may be curved (e.g., circular) or polygonal (e.g., square). In other embodiments, the pinhole collimator 110 may include more than one opening 100. Other types of collimators may also be used in the detector unit 54. Examples of such collimators include, but are not limited to, parallel-hole collimators, slit collimators, slat collimators, converging (e.g. fan-beam) collimators, diverging collimators, and so forth. Selection of a particular collimator may be based on providing optimal usage of the surface (or volume) of the detector assembly 112 for the gamma rays passing through the collimator. In addition, the collimator may be configured to provide an optimal tradeoff between sensitivity and resolution for a wide range of subjects 14.

In the illustrated embodiment, the detector elements 56 are not all oriented in the same direction. For example, an angle 114 indicates an offset from parallel of two of the detector elements 56. As described with respect to FIG. 3, the angle 114 is selected such that the detector unit field of view 86 covers the entire subject 14. Because of the irregular shape of the subject 14, the angle 114 may vary depending on where the detector unit 54 is disposed in the detector arc 50. For example, the angle 114 is larger when the detector unit 54 is placed near relatively flat portions of the subject 14 than when the detector unit 54 is placed near relatively curved portions of the subject 14.

Figure 6:
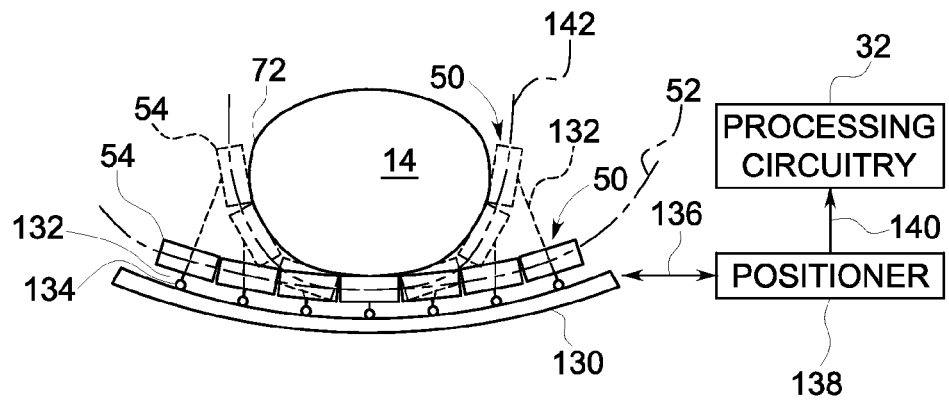
FIG. 6 is a cross-sectional view of an exemplary detector arc conformed to a subject.

FIG. 6 illustrates a cross-sectional view of the detector arc 50 showing how the detector arc 50 conforms to the shape of the subject 14. In the illustrated embodiment, the detector arc 50 is coupled to a detector arc support 130, which supports the detector arc 50 when not in use. Each of the detector units 54 is individually supported by a detector unit support rod 132 coupled to the detector arc support 130. In addition, each of the detector unit support rods 132 is coupled to a sensor/actuator 134, which is disposed on or in the detector arc support 130. Each of the sensors/actuators 134 is configured to extend or retract the detector unit support rod 132, such that the detector units 54 move toward or away from the subject 14. In addition, the sensors/actuators 134 generate signals 136 indicative of the individual positions of the detector units 54. The signals 136 from the sensors/actuators 134 are transmitted to a positioner 138. Thus, each of the detector units 54 is coupled to the positioner 138. Based on the signals 136 from the sensors/actuators 134, the positioner 138 transmits signals 136 to the sensors/actuators 134 to automatically position each of the detector units 54 around the detector arc 50 proximate to the subject 14. In addition, the positioner 138 transmits feedback 140 relating to positions of the detector units 54 to the processing circuitry 32, which uses the feedback 140 in processing the image data. Furthermore, image data from all of the detector units 54 may be collected simultaneously and then transmitted to the processing circuitry 32, which helps to reduce image artifacts and enables dynamic imaging of physiological processes.

In the illustrated embodiment, the detector arc 50 is shown generally aligned with the arc 52 when the detector arc 50 is not in use. In other words, the detector arc support rods 132 are in a retracted state when the detector arc 50 in not in use. Before imaging begins, the sensors/actuators 134 extend the detector unit support rods 132 to position the detector units 54 adjacent to, in close proximity to, or in contact with, the external surface 72 of the subject 14. Thus, the detector arc 50 generally conforms to an in-use arc 142, which varies among different subjects 14, for imaging purposes. As shown in FIG. 6, the in-use arc 142 generally conforms to the shape of the external surface 72 of the subject 14 and is more arcuate than the arc 52. After imaging is complete, the detector unit support rods 132 retract, such that the detector arc 50 conforms to the arc 52. The positioning mechanism for the detector arc 50 described above is one example of how the detector arc 50 may be positioned to conform to the subject 14. In other embodiments, different mechanisms may be used for positioning of the detector arc 50. For example, certain embodiments may include pressure-sensitive sensors or devices to indicate when the detector units 54 have come in contact with the external surface 72.

Figure 7:
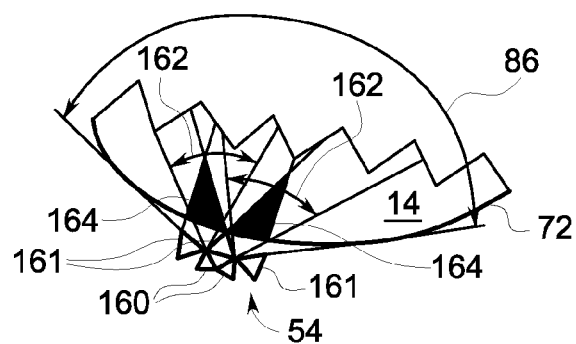
FIG. 7 is a cross-sectional view of a detector unit that includes two rows of detector elements.

FIG. 7 illustrates a cross-sectional view of an embodiment of the detector unit 54 that includes two rows of detector elements. In the illustrated embodiment, a second row of detector elements 160 is disposed behind and between adjacent first row detector elements 161. In other words, each of the second row detector elements 160 is disposed behind and between each of the adjacent first row detector elements 161. Each of the second row detector elements 160 includes a field of view as indicated by angle 162. As shown in FIG. 7, the fields of view of the second row detector elements 160 overlap with the fields of view of the first row detector elements 161. Thus, areas 164 of the subject 14 not included in the fields of view of the first row detector elements 161 are included in the fields of view of the second row detector elements 160. The areas 164 are located in the near portion of the field of view 86. By including the second row detector elements 160, the detector unit field of view 86 includes substantially the entire subject 14, thereby improving angular sampling, spatial resolution, and sensitivity in the near portion of the field of view 86. In other words, the second row detector elements 160 include portions of the subject 14 that may not be imaged because of configuration of the first row detector elements 161.

Figure 8:
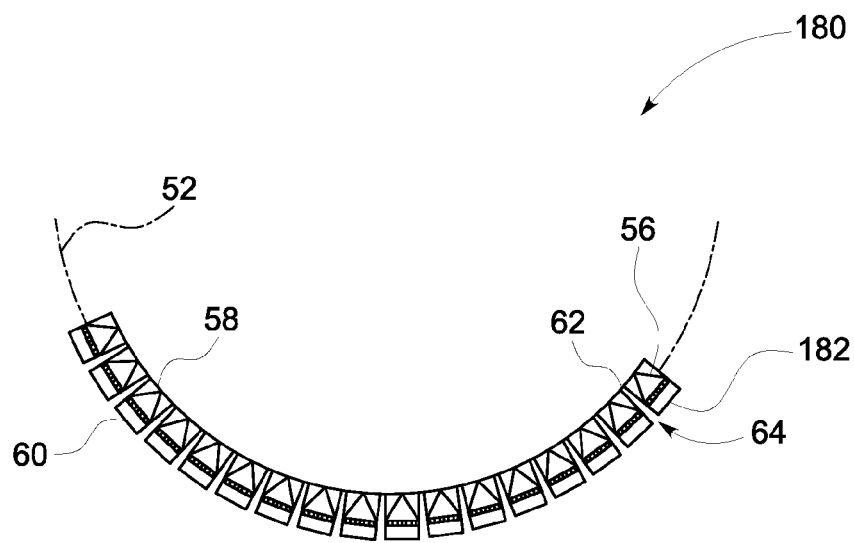
FIG. 8 is a cross-sectional view of an exemplary detector arc that includes a plurality of adjustable detector components.

FIG. 8 illustrates a cross-sectional view of a detector arc 180 that includes a plurality of individually adjustable detector components 182. As with the previously described detector arcs 50, the detector components 182 are adjustably positioned with respect to one another around the detector arc 180. In addition, the detector components 182 generally follow the contours of the arc 52. Furthermore, the individual detector components 182 are interconnected by hinges 62 and are separated by gaps 64. However, unlike the previously described detector arcs 50, each of the detector components 182 includes only one detector element 56. The small size and increased number of detector components 182 may help the detector arc 180 to better conform to the contours of the subject 14. However, unlike the previously described detector arcs 50, each of the detector components 182 does not provide a complete field of view of the subject 14. Instead, the combined fields of view of all of the detector components 182 of the detector arc 180 provide a complete field of view of the subject 14. Mechanisms similar to that described with respect to FIG. 6 may be used for positioning of the detector components 182 adjacent to the subject 14. In addition, a second row of detector components may be disposed behind and between adjacent first row detector components to collect image data not detected by the first row detector components. Furthermore, to help the detector arc 180 provide a complete field of view of the subject 14, not all of the detector components may have the same fields of view. For example, some of the detector components 182 may have a wider field of view than other detector components 182. In other words, at least two of the detector components 182 of the detector arc 180 may have different field of view angles.

Figure 9:
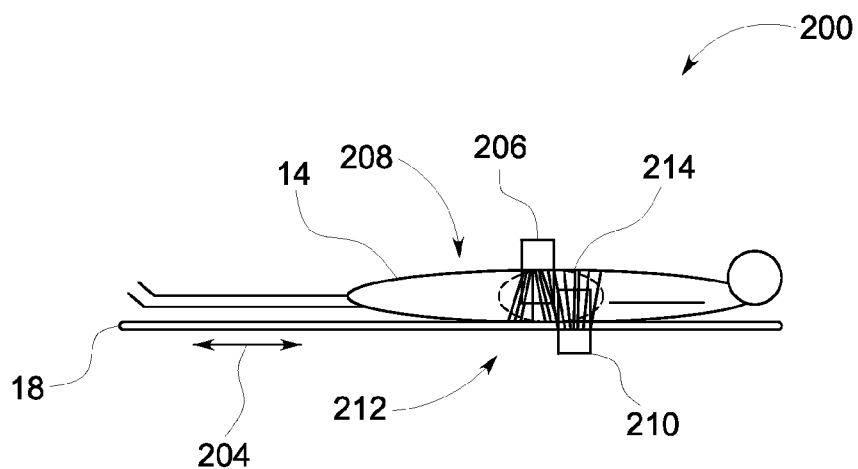
FIG. 9 is a diagrammatical representation of a subject being imaged by two exemplary gamma ray detectors.

FIG. 9 illustrates a diagram of a SPECT detector system 200 that includes more than one detector arc, or gamma ray detector. In the illustrated embodiment, the subject 14 lies on the patient support 18, which may be moved into position as indicated by arrows 204 to place the subject 14 into the field of view of the SPECT system 200. In various embodiments, the subject 14 may be moved continuously through the SPECT detector system or moved in a step and shoot manner. In the illustrated embodiment, the SPECT detector system 200 includes a first gamma ray detector 206 provided on a first side 208 of the patient support 18 and a second gamma ray detector 210 provided on a second side 212 of the patient support 18. Thus, the first and second gamma ray detectors 206 and 210 generally image the subject 14 from opposite directions. In other embodiments, the first and second gamma ray detectors 206 and 210 may not be opposite from one another. In addition, the first and second gamma ray detectors 206 and 210 are axially offset from one another in the illustrated embodiment. Such a configuration may be used when the first and second gamma ray detectors 206 and 210 image more than 180 degrees of the subject 14, such that the first and second gamma ray detectors 206 and 210 cannot be placed directly opposite from one another without interference. In addition, crosstalk between the gamma ray detectors 206 and 210 may be reduced when axially offset. In other embodiments, the first and second gamma ray detectors 206 and 210 may be placed opposite from one another without being axially offset. Use of the first and second gamma ray detectors 206 and 210 provides a combined axial field of view 214 of the subject 14. In addition, the linear motion 204 of the subject 14 may be used to increase the axial field of view 214. In other embodiments, additional gamma ray detectors may be added to the SPECT detector system 200 to further expand the axial field of view 214, increase system sensitivity, and reduce scan times.

Unlike other imaging systems, embodiments of the first and second gamma ray detectors 206 and 210 remain stationary during imaging of the subject 14. Use of stationary first and second gamma ray detectors 206 and 210 provides a number of advantages. For example, the gamma radiation emitted from the subject 14 in all directions may be simultaneously acquired, which helps to reduce image artifacts caused by motion of the subject 14. In addition, simultaneous 3D acquisition provides for dynamic imaging of physiological processes in the subject 14, such as cardiac blood flow dynamics. Use of first and second gamma ray stationary detectors 206 and 210 may simplify and reduce the cost of the SPECT detector system 200. In addition, stationary first and second gamma ray detectors 206 and 210 may help reduce patient discomfort and anxiety. Moreover, the SPECT detector system 200 may provide shorter scan times than other imaging systems, which may also improve patient comfort. Specifically, embodiments of the SPECT detector system 200 provide a complete field of view of the subject, as indicated by the field of view 214 in FIG. 9. Thus, no additional time is needed to rotate or reposition the first and second gamma ray detectors 206 and 210 during imaging of the subject 14.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. A SPECT detector system comprising:
a plurality of detector units, each detector unit comprising a plurality of detector elements disposed in fixed positions with respect to one another, wherein each pair of detector units is separated by a gap; and
a plurality of hinge elements, each hinge element spanning a respective gap to interconnect a respective pair of detector units such that the interconnected detector units are capable of pivoting with respect to one another about the respective hinge element.

2. The system of claim 1, wherein the detector elements of each detector unit are disposed to produce a field of view that covers an entire subject to be imaged.

3. The system of claim 1, wherein the detector elements of at least two of the detector units have different field of view angles.

4. The system of claim 1, wherein the field of view angle of at least one of the detector units is adjustable.

5. The system of claim 1, wherein each detector element comprises a gamma ray sensor and a collimator.

6. The system of claim 5, wherein the collimators of the detector elements comprise pinhole collimators.

7. The system of claim 6, wherein at least one of the detector units comprises a first row of detector elements disposed adjacent to one another and each configured to collect image data over a desired angle, and a second row of detector elements disposed between adjacent first row detector elements and configured to collect image data not detected by the first row detector elements.

8. The system of claim 1, wherein image data from the plurality of detector units is collected substantially simultaneously.

9. A SPECT detector system comprising:
a plurality of gamma ray detectors, at least one first gamma ray detector being provided on a first side of a patient support and at least one second gamma ray detector being provided on a second side of a patient support, each gamma ray detector comprising a plurality of detector units, each detector unit comprising a plurality of detector elements disposed in fixed positions with respect to one another, wherein the detector units are adjustably positioned with respect to one another around a detector arc and are configured to remain stationary during an imaging operation, and wherein the detector elements of each detector unit are disposed to produce a field of view of each detector unit that covers an entire subject to be imaged;
an image data processing component that receives image data from the detector and generates an image based upon the image data.

10. The system of claim 9, wherein the first and second gamma ray detectors are axially offset from one another.

11. The system of claim 9, comprising a detector unit positioner coupled to each of the detector units and configured to automatically position each of the detector units around the detector arc proximate to the subject.

12. The system of claim 11, wherein the detector unit positioner sends feedback relating to positions of the plurality of detector units to the image data processing component.

13. The system of claim 9, wherein the gamma ray detectors are stationary during imaging of the subject.

14. The system of claim 9, wherein each detector element comprises a gamma ray sensor and a collimator.

15. The system of claim 9, wherein the detector units are each separated by a respective gap that is bridged by a respective hinge to allow motion of the detector units with respect to one another.

16. A SPECT detector system comprising:
a plurality of detector components separated from one another by respective gaps and interconnected by hinges that span the gaps such that each detector component is capable of moving independently with respect to the other detector components to allow adjustable positioning of the detector components with respect to one another around a detector arc.

17. The system of claim 16, wherein each detector component comprises at least one gamma ray sensor and at least one collimator.

18. The system of claim 16, the plurality of detector components are disposed to produce a field of view that covers an entire subject to be imaged.

19. The system of claim 16, wherein a first subset of the plurality of detector components is disposed adjacent to one another in a first row and each detector component is configured to collect image data over a desired angle, and wherein a second subset of the plurality of detector components is disposed between adjacent first row detector components in a second row and is configured to collect image data not detected by the first row detector components.

20. The system of claim 16, wherein at least two of the detector components have different field of view angles.

* * * * *